United States Patent
Koscheyev et al.

(10) Patent No.: US 7,089,995 B2
(45) Date of Patent: Aug. 15, 2006

(54) MULTI-ZONE COOLING/WARMING GARMENT

(75) Inventors: Victor S. Koscheyev, Eden Prairie, MN (US); Gloria R. Leon, Minnetonka, MN (US); Michael J. Dancisak, Kenner, LA (US)

(73) Assignee: Regents of the University of Minnesota, Minneapolis, MN (US)

( * ) Notice: Subject to any disclaimer, the term of this patent is extended or adjusted under 35 U.S.C. 154(b) by 384 days.

(21) Appl. No.: 10/143,483

(22) Filed: May 10, 2002

(65) Prior Publication Data

US 2006/0144557 A1    Jul. 6, 2006

Related U.S. Application Data

(60) Provisional application No. 60/290,384, filed on May 11, 2001.

(51) Int. Cl.
*F24J 3/08* (2006.01)
(52) U.S. Cl. .................. 165/45; 607/108; 607/104
(58) Field of Classification Search .............. 165/46; 62/259.3; 607/104–114
See application file for complete search history.

(56) References Cited

U.S. PATENT DOCUMENTS

| | | | |
|---|---|---|---|
| 3,425,486 A * | 2/1969 | Burton et al. ............... 165/46 |
| 3,452,812 A * | 7/1969 | Betts ........................... 165/46 |
| 3,599,625 A | 8/1971 | Curtis |
| 3,610,323 A | 10/1971 | Troyer |
| 3,643,463 A | 2/1972 | Friedlander et al. |
| 3,744,555 A | 7/1973 | Fletcher et al. |
| 4,095,593 A | 6/1978 | Webbon et al. |
| 4,691,762 A | 9/1987 | Elkins et al. |
| 4,738,119 A | 4/1988 | Zafred |
| 5,269,369 A | 12/1993 | Faghri |
| 5,320,164 A | 6/1994 | Szczesuil et al. |
| 5,643,336 A * | 7/1997 | Lopez-Claros ............... 607/104 |
| 5,871,526 A * | 2/1999 | Gibbs et al. ................. 607/104 |
| 5,967,225 A * | 10/1999 | Jenkins ........................ 165/46 |
| 6,109,338 A | 8/2000 | Butzer |
| 6,113,626 A * | 9/2000 | Clifton et al. ................ 607/96 |
| 6,371,976 B1 * | 4/2002 | Vrzalik et al. ............... 607/104 |
| 6,439,942 B1 | 8/2002 | Pillai et al. |

(Continued)

FOREIGN PATENT DOCUMENTS

JP    04209807    7/1992

(Continued)

OTHER PUBLICATIONS

Bader et al., "Indirect Peripheral Vasodilatation Produced by the Warming of Various Body Areas". J Appl Physiol 1:215-226, 1948.

(Continued)

*Primary Examiner*—Terrell McKinnon
(74) *Attorney, Agent, or Firm*—Mueting, Raasch & Gebhardt, P.A.

(57) ABSTRACT

A thermodynamically efficient garment for cooling and/or heating a human body. The thermodynamic efficiency is provided in part by targeting the heat exchange capabilities of the garment to specific areas and/or structures of the human body. The heat exchange garment includes heat exchange zones and one or more non-heat exchange zones, where the heat exchange zones are configured to correspond to one or more high density tissue areas of the human body when the garment is worn. A system including the garment can be used to exchange heat with the adjacent HD tissue areas under the control of a feedback control system. Sensed physiological parameters received by the feedback control system can be used to adjust the characteristics of heat exchange fluid moving within the heat exchange garment.

44 Claims, 7 Drawing Sheets

U.S. PATENT DOCUMENTS

| | | | |
|---|---|---|---|
| 6,500,200 B1 * | 12/2002 | Kushnir | 607/104 |
| 6,551,347 B1 * | 4/2003 | Elkins | 607/104 |
| 6,551,348 B1 * | 4/2003 | Blalock et al. | 607/104 |
| 6,685,731 B1 | 2/2004 | Kushnir et al. | |
| 2002/0096311 A1 | 7/2002 | Kushnir et al. | |
| 2003/0069621 A1 | 4/2003 | Kushnir | |
| 2004/0078864 A1 | 4/2004 | Miros et al. | |

FOREIGN PATENT DOCUMENTS

| | | |
|---|---|---|
| WO | 09937174 | 7/1999 |

OTHER PUBLICATIONS

Bavro et al., "Optimization of the Human Body Topography for Warming the Organism in a Cold Environment". Occupational Health, 1976, 9:22-25 (Russian).

Brajkovic et al., "Influence of localized auxiliary heating on hand comfort during cold exposure". J App Physiol 85(6): 2054-2065, 1998a.

Brajkovic et al., "The Effects of Clothing Insulation and Levels of Torso Heating on Finger Dexterity". Paper Presentation at the 8th International Conference on Environmental Ergonomics. pp. 219-222, Oct. 21, 1998. San Diego, California, (1998b).

Burton et al., "Man in a Cold Environment". Edward Arnold (Publishers) LTD. London 1955—(Cover Page and Table of Contents).

Cadarette et al. "Evaluation of Three Commercial Microclimate Cooling Systems". Aviat Space Environ Med 1990; pp. 71-76.

Cheung et al., "Development of a Novel Thermal Control Suit for Human Thermoregulation and Environmental Ergonomic Studies". Proceedings of the Australian Physiological and Pharmacological Society (2001) 32(2) Suppl 1, pp. 16P.

Clemente, "Anatomy: A Regional Atlas of the Human Body". 4th ed. Baltimore: Williams and Wilkins, 1997. (Table of Contents).

Coca et al., "Assessment in Humans of Heat Exchange at Specific Body Areas Using a Multi-Compartment Liquid Cooling/Warming Garment". Proceedings of the Australian Physiological and Pharmacological Society (2001) 32 (2) Suppl 1, 17P.

DuBois et al., "A Formula to Estimate the Approximate Surface Area If Height and Weight Be Known". Arch Intern Med. 17:863-871, 1916.

Ducharme et al., "Role of Blood as Heat Source or Sink in Human Limbs During Local Cooling and Heating". J Appl Physiol 76(5):2084-2094, 1994.

Ducharme et al., "Tissue Temperature Profile in the Human Forearm During Thermal Stress at Thermal Stability". J Appl Physiol 71(5):1973-1978, 1991.

Elbakyan et al., "The Automatic Thermal Control System (ATCS) for the EVA Space Suit". SAE Technical Paper Series 941382. In Proceedings of the 24th International Conference on Environmental Systems and 5th European Symposium on Space Environmental Control Systems, Friedrichshafen Germany Jun. 20-23, 1994, pp. 1-13.

Froese et al. "Heat Losses From the Human Head". I Appl. Physiol 1957; 10(2):235-41.

Goldman, "The Arctic Soldier—Possible Research Solutions for His Protection". In Science in Alaska: Dahlgren G (ed), Proceedings of the 15th Alaskan Science Conference College, Alaska, Aug. 31 to Sep. 4, 1964 American Association for the Advancement of Science, Washington, Mar. 15, 1965, pp . 401-422.

Gonzales et al., "Thermoregulatory Responses to Cold: Effects of Handwear With Multi-Layered Clothing". Aviat, Space, Environ Med 69(11): 1076-1082.

Gwosdow et al., "Physiological and Behavioral Temperature Regulation of Men in Simulated Nonuniform Thermal Environments Between 18 and 30° C". Aviat, Space, Environ Med 60:558-565, 1989.

Hayami et al., "Cooling Effects on Muscular Activity". J. Anthropol Soc Jap 756:201-205. 1967.

Heising et al., "Differential Heating of Trunk and Extremities". Eur J Appl Physiol 54: 79-83, 1985.

Hoffman et al., "Experimental Hypothermia and Cold Perception". Aviat, Space, Environ Med 60: 964-969, 1989.

Hong et al., "Peripheral Blood Flow and Heat Flux of Korean Women Divers". Federation of American Societies for Experimental Biology. vol. 28: No. 3, 1143-1148, 1969.

Hughes, "Canadian Helicopter Pilots Use Icewater Vests and New Chemical Masks Over Persian Gulf". Aviation Week & Space Technology, Jan. 7, 1991, p. 55.

Koscheyev et al., "Forced and Directed Heat Exchange for Providing Human Body Comfort in Extreme Environments". SAE Technical Paper Series 972318. Proceedings of the 27th International Conference on Environmental Systems, Jul. 14-17, Lake Tahoe, Nevada. SAE International, Warrendale, PA., USA, pp. 1-8, 1997.

Koscheyev et al., "Body Surface Temperature Tuning as a Comfort Support System in Space and Other Extreme Environments". SAE Technical Paper Series 981723. In Proceedings of the 28th International Conference on Environmental Systems. Jul. 13-16, Danvers, MA. SAE International, Warrendale, PA., USA, pp. 1-8, 1998.

Koscheyev et al., "Maximal Conductive Heat Exchange Through Different Body Zones in a Liquid Cooling/Warming Space Garment". Paper No.-001CES-385, 30th International Conference on Environmental Systems, Toulouse, France. Jul. 10-13, 2000. 2000 Society of Automotive Engineers, Inc.

Koscheyev, "Physiologic and Hygienic Individualized Protection for Persons in Extreme Cold". Moscow: Medicine, 1982. (Russian).

Koscheyev et al., "Thermoregulation and Heat Exchange in a Nonuniform Thermal Environment During Simulated Extended EVA". Aviat, Space, Environ Med, Jun. 2000: vol. 71, No. 6:579-85.

Koscheyev et al., "Augmentation of Blood Circulation to the Fingers by Warming Distant Body Areas". Eur. J. Appl. Physiol (2000), 82:103-111.

Koscheyev et al., "Augmentation of Blood Circulation to the Fingers Through Wrist Warming to Enhance Finger Comfort During Long-Duration EVA". SAE Technical Paper Series 1999-01-1969. In Proceedings of the 29th International Conference on Environmental Systems, Jul. 10-14, 1999, Denver, Colorado.

Koscheyev et al., "Efficacy of Wrist/Palm Warming as an EVA Countermeasure to Maintain Finger Comfort in Cold Conditions". Aviation, Space, and Environmental Medicine, vol. 72, No. 8, Aug. 2001, pp. 713-719.

Koscheyev et al., "Approaches to Monitoring Thermal Status in Humans Under Nonuniform Heating/Cooling on the Body Surface". Proceedings of the Australian Physiological and Pharmacological Society (2001), 32 (2) Suppl 1, 84P.

Koscheyev et al., "Individual Thermal Profiles for Human Comfort Management in Extreme Environments". Proceedings of the 8th International Conf. On Environmental Ergonomics, San Diego, CA, Oct. 18-23, 1998.

Koscheyev et al., "Improvements in Comfort and Thermal Status Control of Astronauts During Extra Vehicular Activities (EVA): Achievements and Perspectives". #405, Asthma 2002 Meeting Abstracts, Aviation, Space and Environmental Medicine, vol. 73, No. 3, Mar. 2002, p. 303.

Koscheyev et al., "Comfort and Heat Control During Extended Space Flights". In: Proceedings of the 26th International Conf. On Environmental Systems, Monterey, California, Jul. 8-11, 1996: SAE Technical Paper Series 961538. pp. 1-5.

Koscheyev et al., "Physiological Approaches for the "Smart Design" of a Cooling/Warming Garment for Routine and Emergency EVA", Poster presented at Bioastronautics Investigators Workshop, Galveston, Texas, Jan. 2001.

Ku et al., "Hemodynamic and Thermal Responses to Head and Neck Cooling in Men and Women". Am J Phys Med Rehabil 1996: 75:443-450.

Kuznetz, "Automatic Control of Human Thermal Comfort by a Liquid Cooling Garment". J Biomech Engin 1980; 102: 155-161.

McLellan et al., "Efficacy of Air and Liquid Cooling During Light and Heavy Exercise While Wearing NBC Clothing". Aviat, Space, Environ Med 1999; 70(8): 802-811.

Merrill et al., "Automatic temperature Control for Liquid-Cooled Flight Suits", U.S. Naval Air Development Center, Johnsville, Warminster, Pennsylvania. Progress Report, Bureau of Medicine & Surgery, Work Unit MF022.02.02-6001 Aug. 3, 1967.

Montgomery et al. "Effect of Ambient Temperature on the Thermal Profile of the Human Forearm, Hand and Fingers". Annals Biomedical Eng 1976; 4:209-219.

Montgomery et al. "Variation of Forearm, Hand and Finger Blood Flow Indices with Ambient Temperature". Aviat, Space, Environ Med 1977; 48(3):231-5.

Nyberg et al., "Automatic Thermal Control through a LCVG for a Spacesuit". 1998 Society of Automotive Engineers, Inc. ES27, 99ES-152.

Rapaport et al., "Control of Blood Flow to the Extremities at Low Ambient Temperatures". J Appl Physiol 2:61-71, 1949.

Santee et al., "Comparison of Issue and Prototype Lightweight Chemical Protective Undergarments and Overgarments", AsMA 2002 Meeting Abstracts, #281, Aviation, Space and Environmental Medicine, vol. 73, No. 3, Mar. 2002, p. 277.

Shvartz. "Efficiency and Effectiveness of Different Water Cooled Suits—A Review". Aerosp Med 1972; 43(5):488-491.

Toner et al., "Physiological Adjustment of Man to the Cold". In: Pandolf KB, Sawka MN, Gonzalez RR (eds) Human Performance Physiology and Environmental Medicine at Terrestrial Extremes. Benchmark Press Inc., Indianapolis. pp. 361-399, 1986.

Vallerand et al. "Heat Balance of Subjects Wearing Protective Clothing with a Liquid of Aircooled Vest", Aviat, Space, Environ Med 1991: 62(5):383-91.

Webb et al., "Automatic Cooling in Water Cooled Space Suits". Aerospace Med. 1970; 41(3):269-277.

Webb, et al., "Human Calorimetry with a Water-Cooled Garment". J Appl Physiol, vol. 32, No. 3, Mar. 1972. pp. 412-418.

Werner et al., "Consequences of Partial Body Warming and Cooling for the Drives to Local Sweat Rates". Eur J Appl Physiol 60: 300-304, 1990.

Xu et al., "Multi-Loop Control of Liquid Cooling Garment Systems". Ergonomics, 1999. vol. 42, No. 2, 282-298.

Young et al., "Cooling Different Body Surfaces During Upper and Lower Body Exercise". J Appl Physiol. 63(3): 1218-1223, 1987.

Zaratuichenko et al., "Human Thermoregulation Model for Space Suit: Mathematical Model for Human Thermal Regulation in a Suited Mode with Ventilation and Liquid Cooling Capabilities Provided", SAE Technical Paper Series, #972319, 27th International Conference on Environmental Systems, Lake Tahoe, NV., Jul. 14-17, 1997. pp. 1-12.

* cited by examiner

MULTI-ZONE COOLING/WARMING GARMENT

This application claims the benefit of U.S. Provisional Application Ser. No. 60/290,384, file 11 May 2001, which is incorporated herein by reference in its entirety.

STATEMENT OF GOVERNMENT RIGHTS

The present invention was made with support from the National Aeronautics and Space Administration (NASA) under NASA Grant No. NAG9-1218. The government may have certain rights in this invention.

TECHNICAL FIELD

The present invention relates generally to liquid cooling/warming garments. More particularly, the present invention pertains to physiologically based garments and methods/systems for liquid cooling/warming of, for example, a human.

BACKGROUND

When operating normally, the core temperature of the human body is regulated somewhere between 98° F. and 100° F. The body uses a variety of heat transfer mechanisms in regulating its core temperature. These heat transfer mechanisms include radiation, conduction, convection and evaporation of water from the body.

When the environmental temperature is below the body temperature, heat is transferred from the body through one or more heat transfer mechanisms of radiation, conduction, convection and/or evaporation of water from the body. This forces the body to conserve heat and increase heat production. When the environmental temperature is above the body temperature, heat is transferred into the body through one or more heat transfer mechanisms of radiation, conduction, and/or convection. In this situation, for example, the body uses the evaporation of perspiration from the skin and the evaporative cooling from exhaled moisture to maintain the core body temperature.

The body takes an active role in regulating the body temperature. The temperature of the body is regulated by neural feedback mechanisms that operate primarily through the hypothalmus. The hypothalmus contains not only the control mechanisms, but also the key temperature sensors. Under control of these mechanisms, sweating begins almost precisely at a skin temperature of 35° C. and increases rapidly as the skin temperature rises above this value. The heat production of the body under these conditions remains almost constant as the skin temperature rises. If the skin temperature drops below 35° C., a variety of responses are initiated to conserve the heat in the body and to increase heat production. These include vasoconstriction to decrease the flow of heat to the skin, cessation of sweating, shivering to increase heat production by the muscles and the secretion of norepinephrine, epinephrine, and thyroxine to increase heat production.

Different regions of the body have different abilities to transfer heat. This is based in part on both the surface area of the body region and the relative vascularization of the body region. For example, up to 40% of the body's heat is lost from the head. This is due to the large blood supply to the head, the extra surface area of the head, and from water evaporating from the nose and mouth. Other areas where there is a large muscle mass also coupled with a large surface area also can lose a significant amount of heat.

Clothing is used to help maintain the body core temperature. For example, additional layers of clothing are worn to help maintain body temperature in cold environments. Conversely, fewer layers of clothing are worn to help maintain body temperature in warmer environments. Regulating body temperatures due to a change in a person's activity level in these conditions is usually as simple as adding or subtracting additional layers of clothing.

In some situations, the person is unable to remove or add additional layers of clothing when their activity level changes. For example, people working in very hostile environments are not able to remove or add to their protective clothing and/or suits if they become too hot or cold (e.g., astronauts, fighter pilots, firemen, divers, etc.). In some situations it is also possible that a person can be too warm in one region of their body, while another region is too cold.

Garments for controlling the core body temperature have been suggested. These garments typically have a system for circulating temperature controlling fluid into and out of the garments, e.g., via tubes positioned in the garment. The temperature controlling fluid is generally circulated through the entire garment, regardless of whether the body area needs to be heated or cooled. In doing so, the system wastes energy. For example, energy is wasted in pumping temperature controlling fluid that may not be needed in a particular area of the suit. In addition, the efficiency of the system is reduced. Reduced efficiency results when areas that may require more heating or cooling fail to receive sufficient temperature controlling fluid to control the body temperature because a portion of the finite amount of temperature controlling fluid may be circulating in areas that do not require heating or cooling at that time. Furthermore, the garments used to control temperature of the body are generally heavy and cannot be worn for long periods of time.

SUMMARY OF THE INVENTION

The present invention provides a thermodynamically efficient garment for cooling and/or heating a human body. The thermodynamic efficiency is provided in part by targeting the heat exchange capabilities of the garment to specific areas and/or structures of the human body. The present invention identifies these specific areas and/or structures of the human body based on an evaluation of their effectiveness in transferring heat. These specific areas and/or structures of the human body include not only areas of high blood vessel distribution, but also areas of high tissue conductivity. These areas of high tissue conductivity are also referred to herein as areas of high-density tissue. Recognizing and using these areas of high tissue conductivity for heat transfer allows for a smaller more efficient garment for cooling and heating the human body as compared to other heat exchange garments.

The present invention introduces the concept of high density (HD) tissue for use in heat transfer to and from the human body. HD tissue includes discrete areas of the human body that have a higher efficiency in transferring heat to or from the body than other non-HD tissue areas of the body. Generally, HD tissue has been found to have superior blood vessel distribution, heat conductivity, and heat transport capability to and from the blood. The present invention makes use of the HD tissue to allow a lighter, more compact garment for heat transfer than has been known.

HD tissues are located in different regions of the body, but all share common major characteristics. These major characteristics include, but are not limited to, discrete areas of the body that have a high cell density or compact mineral content as compared to other body tissues, areas that include more than one of bone, tendon, fascia and muscle tissues types in close proximity to both the skin and to major vascular structures of the body, and that display high coefficients of conductivity. These high coefficients of conductivity are due in part to the body tissues that make up the HD region of the body (e.g., bone, tendon, fascia, muscle).

The present invention uses both HD tissue and non-high density tissue in controlling the temperature and comfort of the human body. A heat exchange garment is provided, where the heat exchange garment comprising at least one heat exchange zone and one or more non-heat exchange zones. In one embodiment, the at least one heat exchange zones are configured to correspond to one or more HD tissue areas of the human body. Each of the heat exchange zones further comprises heat exchange elements for use in transferring at least heat to the human body. Preferably, the location of heat exchange elements in the garment are located substantially only in the at least one heat exchange zone.

In one embodiment, the heat exchange zones of the heat exchange garment can be positioned to be adjacent one or more HD tissue areas of the body. The areas of the HD tissue preferably include high levels of vascularization. Heat can then be transferred between heat exchange zones of the heat exchange garment and the adjacent HD tissue areas of the body. The heat exchange can include providing cooling or heating to the adjacent HD tissue areas. In one embodiment, one or more adjacent HD tissue areas can be cooled, while one or more additional adjacent high density tissue areas can be heated.

In one embodiment, heating and cooling of the HD tissue regions of the body can be in an effort to provide thermal comfort to the person wearing the heat exchange system of the present invention. Thermal comfort can be accomplished by balancing the heating and cooling requirements of different HD tissue regions of the body. In one embodiment, this balancing can be accomplished by using one or more sensed physiological parameters in a feedback control system. Based on the sensed physiological parameters, at least one characteristic of a heat exchange fluid within a heat exchange garment can be controlled based on the sensed one or more physiological parameters.

BREIF DESCRIPTION OF FIGURES

FIGS. 6A, 6B, 6C, and 6D is a schematic diagram illustrating various embodiments of a portion of a heat exchange garment according to one embodiment of the present invention.

Figure 7:
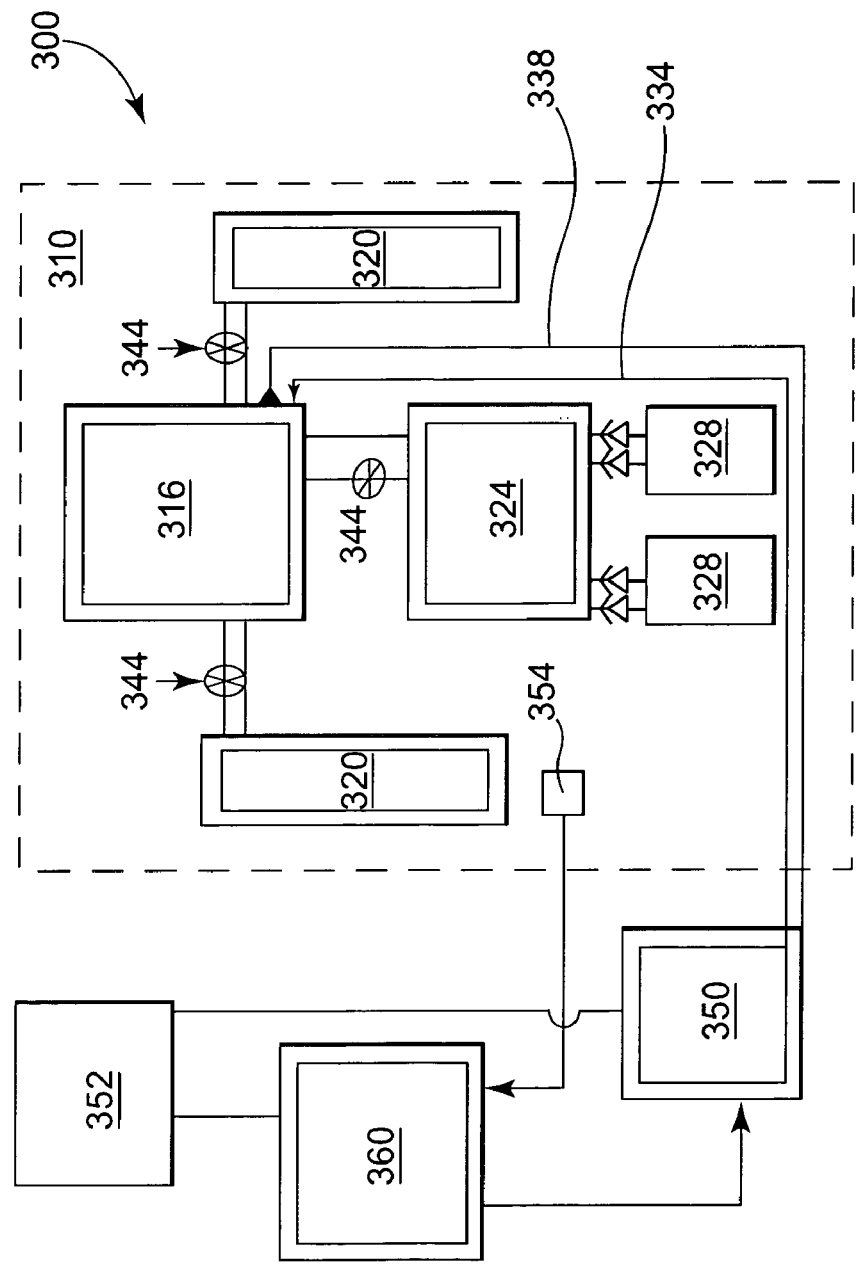

FIG. 7 is a block diagram of a heat exchange system according to one embodiment of the present invention.

DETAILED DESCRIPTION

In the following detailed description of the embodiments, reference is made to drawings that form a part hereof, and in which are shown by way of illustration specific embodiments in which the invention may be practiced. It is to be understood that other embodiments may be utilized and processing step/structural changes may be made without departing from the scope of the present invention.

The present invention provides a thermodynamically efficient garment for cooling and/or heating a human body. The thermodynamic efficiency is provided in part by targeting the heat exchange capabilities of the garment to specific areas and/or structures of the human body. The present invention identifies these specific areas and/or structures of the human body based on an evaluation of their effectiveness in transferring heat. These specific areas and/or structures of the human body include not only areas of high blood vessel distribution, but also areas of high tissue conductivity. These areas of high tissue conductivity are also referred to herein as areas of high-density tissue, and will be discussed more fully below. Recognizing and using these areas of high tissue conductivity for heat transfer allows for a smaller more efficient garment for cooling and heating the human body as compared to other heat exchange garments.

Generally, the garment for cooling and heating of the present invention includes two or more zones for exchanging heat with the human body. In one example, each of the two or more zones includes a closed loop system in which a fluid can be used to exchange heat with the body. The fluid can then exchange the transferred heat with a heat sink reservoir. Each of the two or more zones is specifically tailored to exchange heat with one or more specific areas of high tissue density in the body. Tailoring the zones to these specific areas allows for a smaller heat exchange area for a given quantity of heat transfer as compared to conventional heat exchange garments for the comparable quantity of heat transfer. This is due in part to the recognition that high-density tissue areas have the ability to more efficiently transfer heat as compared to other tissue areas. Less heat exchange surface area results in smaller more efficient heat exchange garments for cooling and heating the human.

The more efficient the heat transfer, the smaller the area of the garment that is required to heat and/or cool the body area. These smaller areas result in a heat exchange garment that is lighter and more energy efficient than conventional heat exchange garments. For example, because the heat exchange garment of the present system is smaller than conventional systems due to its increased efficiency, there is less heat exchange fluid and tubing required for heat exchange. This results in a lighter heat exchange garment. In addition, since a smaller volume of fluid can be required for the heat exchange, the amount of heat transferred to or from the body for a given volume of fluid is increased. Thus, the energy to move the fluid in the heat exchange garment is more efficiently used than in conventional methods of heat exchange.

The garment of the present invention can also include a shunting system between each of the two or more compartments of the garment. The shunting system provides for controlling a volume of fluid flow in one or more of the compartments of the garment. The shunting system can be used to stop or reduce the volume of fluid moving in one or more compartments of the garment. The shunting system can be activated either manually, and/or through an automatic feedback system of the heat exchange garment. In certain situations, minimal heating or cooling requirements for a person wearing the garment of the present invention can be attained by closing off or reducing the flow to one or more compartments of the garment through the use of the shunts. Adjusting the fluid flow in this way creates an effectively shorter tube pathway that places less of a demand on the heat exchange system of the present invention.

The garment of the present invention also allows for body heat to be balanced. Balancing body heat with the garment of the present invention includes providing heating to one or more compartments of the garment, while simultaneously providing cooling to one or more separate compartments of the garment. Balancing body heat can include attempting to maintain a uniform temperature across the body. For example, balancing body heat can include removing heat from the torso of a person's body, while simultaneously providing heat to the periphery (such as fingers and/or toes) of the person's body. Other examples will be discussed below.

The present invention introduces the concept of high density (HD) tissue for use in heat transfer to and from the human body. HD tissue includes discrete areas of the human body have a higher efficiency in transferring heat to or from the body than other non-HD tissue areas of the body. Generally, HD tissue has been found to have superior blood vessel distribution, heat conductivity, and heat transport capability to and from the blood. The present invention makes use of the HD tissue to allow a lighter, more compact garment for heat transfer than has been known. Examples of the garment for heat transfer are provided below.

In one embodiment, HD tissue can be defined based on the density of cells making up the body tissue along with the amount of vascluarization present in the body tissue. Tissues having a HD designation include a threshold number of cells per unit volume of tissue. Examples of HD tissue include, but are not limited to regions of bone, tendon, and/or fascia, positioned proximal to the skin. HD tissues can also include muscle, where the muscle is highly vascularized (intensive circulation). Preferably, the HD tissues are regions of the body that include more than one of these types of tissues (e.g., bone, tendon, fascia, muscle).

In addition, HD tissues in general can include high levels of vascularization. For example, areas of HD tissue typically include major arteries and/or veins in or adjacent to the HD tissue. In one embodiment, blood flowing in the major arteries and/or veins in or adjacent to the HD tissue transfers heat to and from the HD tissue. The blood flowing in the major arteries and/or veins in or adjacent to the HD tissue can then be used to transfer heat directly from or into the heat exchange fluid in the garment.

Specific areas of the body have been identified as having HD tissue. These areas include, but are not limited to the forearm, wrist, lateral thoracic area (also referred to as the rib cage), upper torso, paraspinal areas, occipital and parietal head areas, gluteal and medial or inner thigh, shoulder, pectoral region, ankle, and groin area. Different combinations of these areas can be used in providing the efficient heat transfer of the present invention.

The two or more compartments of the present invention can be targeted to the HD tissue areas of the body. In this way, heat exchange between the compartments of the garment and the body can be accomplished more efficiently. Table 1 provides examples of coefficient of heat conductivity and tissue density for different tissue types, including HD tissues and non-HD tissues.

TABLE 1

| Body tissues with different blood circulation intensity | Coefficient of conductivity, (W/m*K) | Density, (g/cm$^3$) |
|---|---|---|
| Skin (weak circulation) | 0.147 ± 34% | 1.085 ± 0% |
| Skin (intensive circulation) | 0.314 | |
| Fat | 0.187 ± 17% | 0.92 ± 0% |
| Muscle (weak circulation) | 0.461 ± 27% | 1.062 ± 4% |
| Muscle (normal circulation) | 0.533 | |
| Muscle (intensive circulation) | 0.628 | |
| Bone | 0.782 ± 46% | 1.357 ± 0% |

As will be noted, bone displays the highest coefficient of heat conductivity of the body tissues listed in Table 1. In addition, bone also displays the highest density of the body tissues listed in Table 1. Both the coefficient of heat conductivity and the density are important factors in the heat transfer characteristics of the HD tissue. In addition, when the HD includes not only bone, but also includes muscle having intensive circulation, such as in the lateral thoracic (rib cage) area and/or shoulder area, there is an increase in the overall coefficient of conductivity, and therefore the ability to exchange heat with the body.

The HD tissue areas of the body are also typically highly vascularized. For example, the lateral thoracic (rib cage) area and/or shoulder area include the common carotid artery, the subclavian artery, suprascapular and subscapular artery, and interior, lateral thoracic artery, exterior jugular veins, lower subclavian veins, and the axillary vein including both the brachial and cephalic veins. Other arteries and veins are also useful in heat exchanges with the garment of the present invention, and the foregoing list of arteries is only exemplary, and not intended to be limiting. Thus, it is preferred that the HD tissue also includes sufficient adjacent vascularization that allows for efficient heat transfer to and from the body.

Thus, HD tissues are located are different regions of the body, but all share common major characteristics. These major characteristics include, but are not limited to, discrete areas of the body that have a high cell density as compared to other body tissues, areas that include more than one of bone, tendon, fascia and muscle tissue types in close proximity to both the skin and to major vascular structures of the body, and that display high coefficients of conductivity. These high coefficients of conductivity are due in part to the body tissues that make up the HD region of the body (e.g., bone, tendon, fascia, muscle). In one embodiment, the HD tissues preferably have a coefficient of conductivity of at least 0.5 (W/m*K). More preferably, the HD tissues preferably have a coefficient of conductivity of at least 0.8 (W/m*K). It is also possible that the HD tissues have a coefficient of conductivity in a range of 0.5 to approximately 0.8 (W/m*K).

Other areas were identified as not exhibiting HD tissue characteristics. These areas include, but are not limited to, areas having large muscle groups with reduced vascularization. Examples of these non-HD tissues include, but are not limited to, those of the thigh (e.g., rectus gemoris, vastus lateralis, gracilis, and biceps muscles), the stomach (e.g., transverses, rectus abdominis, linea alba, and interior and exterior oblique muscles), and buttocks (e.g., gluteus maximus). These areas of the body typically exhibit a larger percentage of the body surface area. Surprisingly, however, these areas have less intensive heat dissipation as compared to HD tissues because of their lower tissue conductivity coefficients. High thermal insulation and low thermal conductivity compared to other body tissues reduce the non-HD tissues effectiveness in transporting heat.

These areas of the body can exhibit a combination of features that lead them to being non-HD tissue. For example, the features can include, but are not limited to, exhibiting a high thermal insulation due in part to insufficient vascularization for rapid heat transfer. The high thermal insulation can also be due to the presence of a fat layer over the muscle structure that adds more significantly to the thermal insulation than thermal conductivity of the area, especially in rest conditions. These areas of the body typically have a thicker fat layer as compared to those in the HD tissue area. The presence of the fat layer adds to the high thermal insulation characteristics (e.g., low thermal conductivity) of the non-HD tissue area. Also, blood impregnation of the leg and buttock surface from the deep vessels networks occurs slowly, because the network is not as highly developed for this function as the distal parts of extremities. Therefore, heat is not distributed quickly through blood to the surface of the thigh. Understanding the differences in tissue conductivity and structure between HD and non-HD tissue allows for smaller more efficient heat exchange garments to be created as compared to other heat exchange suits.

Figure 1:
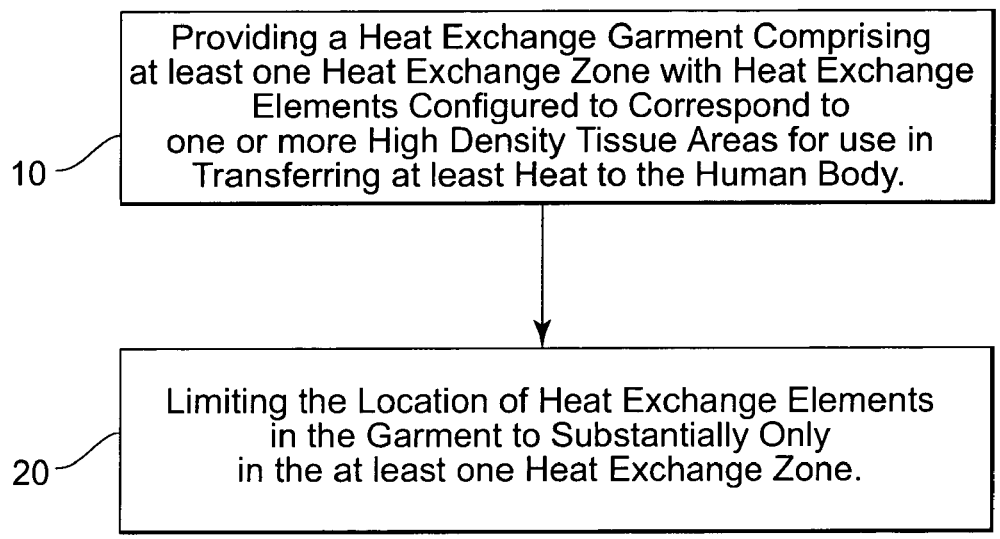
FIG. 1 is a flow chart illustrating a technique for controlling body temperature according to one embodiment of the present invention.

FIG. 1 provides one example of a method for controlling body temperature according to the present invention. At 10, a heat exchange garment is provided that includes at least one heat exchange zone configured to correspond to one or more high density tissue areas of a human body. As will be described more fully below, each heat exchange zone comprises heat exchange elements for use in transferring at least heat to the human body.

At 20 of FIG. 1, the location of heat exchange elements in the garment is limited to substantially only in the at least one heat exchange zone. So, the at least one heat exchange zone of the heat exchange garment is substantially only positioned adjacent one or more HD tissue areas of the body. In one example, each of the heat exchange zones can be located in predetermined regions of the heat exchange garment. When the garment is then worn on the human body, each of the at least one heat exchange zones can be positioned adjacent the HD tissue sites of the human body.

In one example, the at least one heat exchange zones can be positioned adjacent the HD tissue sites located in or through any number of body planes. These body planes include, but are not limited to, the superior and/or inferior portions of the transverse plane, and/or the posterior and/or anterior portions of the coronal plane. In addition, the at least one heat exchange zones can be located on bilateral portions, or contralateral portions, of the HD tissue areas of the body. For example, the at least one heat exchange zones can include at least a first heat exchange zone and a second heat exchange zone, where the first heat exchange zone can be located on a left lateral thoracic area and the second heat exchange zone can be located on a right lateral thoracic area when the garment is worn.

Additional heat exchange zones (e.g., third heat exchange zone, fourth heat exchange zone, etc) can also be included on the heat exchange garment. These additional heat exchange zones can also be located adjacent HD tissue in any of the above mentioned body planes and bilateral portions of the body. For example, in addition to the first and second heat exchange zones located on the bilateral portions of the lateral thoracic area, additional heat exchange zones (e.g., third and fourth heat exchange zones) can be located adjacent additional HD tissue areas of the body. In one embodiment, the third and fourth heat exchange zones can be located on the left forearm and the right forearm, respectively, of the human body. Alternatively, the third and fourth heat exchange zones could include other bilateral portions of the HD tissue described above. It is also recognized that additional heat exchange zones could be located on any combination of HD tissue areas (bilateral or not bilateral) described for the present invention. As will be discussed more fully below, each of the heat exchange zones located with respect to the garment also includes one or more heat exchange elements.

The heat exchange element can be used to exchange heat between the at least one heat exchange zones of the heat exchange garment and the adjacent HD tissue areas of the body. In one example, the heat exchange element is tubing that uses heat exchange fluid to exchange heat between the heat exchange zone and the adjacent HD tissue area of the body. For example, heat exchange fluid can be pumped through the heat exchange element, where depending in part upon a temperature gradient between the heat exchange fluid and the adjacent HD tissue, heat either flows from the heat exchange fluid to the adjacent HD tissue or flows from the adjacent HD tissue to the heat exchange fluid.

In one embodiment, the heat exchange element can be used to cool the HD tissue area adjacent a heat exchange zone of the heat exchange garment. In addition, more than one heat exchange zone could be used to cool HD tissue areas of the body. Similarly, the heat exchange element can be used to heat the HD tissue area adjacent a heat exchange zone of the heat exchange garment. In addition, more than one heat exchange zone can also be used to heat HD tissue areas of the body.

Alternatively, exchanging heat with the heat exchange elements can include cooling and heating different HD tissue areas. For example, a heat exchange element in the first heat exchange zone can be used in cooling a first adjacent HD tissue area, while a heat exchange element in the second heat exchange zone can be used in heating a second adjacent HD tissue area. The heating and cooling by the heat exchange elements can occur substantially simultaneously during the same time interval or can occur during independent time intervals, e.g., sequentially.

Different combinations of heating and cooling multiple HD tissue areas are also possible. For example, first and second heat exchange zones can be positioned adjacent bilateral portions of a first HD tissue area, while third and fourth heat exchange zones can be positioned adjacent bilateral portions of a second HD tissue area. In this situation, the heat exchange elements in the first and second heat exchange zones can be used to cool the bilateral portions of the first HD tissue area, while the heat exchange elements in the third and fourth heat exchange zones can be used to heat the bilateral portions of the second HD tissue area. Adding additional heat exchange zones for combinational heating and/or cooling of additional HD tissue areas is also possible.

In addition, substantially simultaneous heating and cooling of different halves of bilateral portions of a HD tissue area is also possible. For example, a bilateral HD tissue area having a first and a second HD tissue area can have the first HD tissue area being cooled with a first heat exchange zone, while the second HD tissue area is being heated with a second heat exchange zone. This option can be useful when the first HD tissue area and the second HD tissue area are experiencing contrasting levels of heat flux. For example, heat flux differences can exist when the first HD tissue area is exposed to a heat source (e.g., facing the sun), while the second HD tissue area is not exposed to the heat source (e.g., shaded from the sun).

Figure 2:
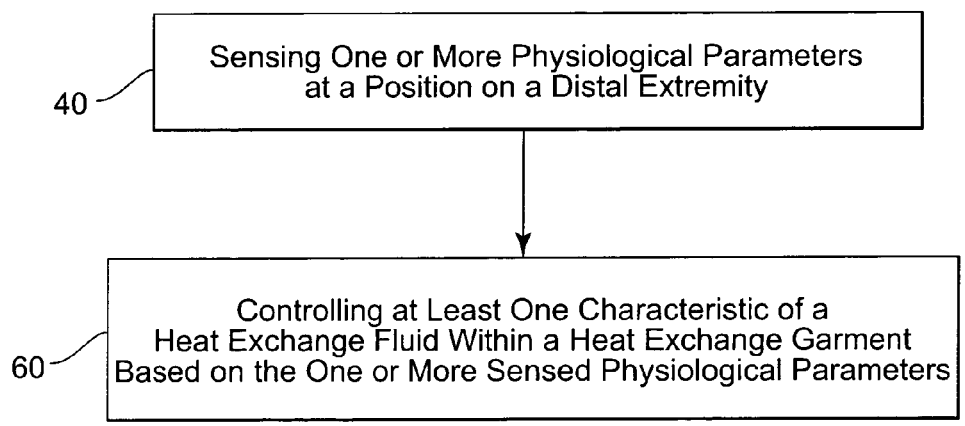
FIG. 2 is a flow chart illustrating an additional technique for controlling body temperature according to one embodiment of the present invention.

FIG. 2 shows an additional embodiment of a method for controlling body temperature according to the present invention. At 40, one or more physiological parameters are sensed, e.g., at a position on a distal extremity of the human body. These physiological parameters can include, but are not limited to, skin temperature, heat flux, blood perfusion and skin wetness data. In one embodiment, the position on the distal extremity of the human body is monitored. This position on the distal extremity can include any number of locations. In one example, one or more fingers are used as the distal extremity from which the physiological parameters are sensed. In an additional example, the ear canal is used as the position on a distal extremity from which the physiological parameters are sensed. Alternatively, additional or alternative physiological parameters can be sensed from the dorsal surface of one or both hands.

At 60, based on one or more of the sensed physiological parameters, at least one characteristic of the heat exchange fluid in the heat exchange garment can be controlled. For example, controlling at least one characteristic of the heat exchange fluid can include controlling a flow rate of the heat exchange fluid within the heat exchange garment based on the sensed physiological parameters. So, for example, when the heat exchange garment includes heat exchange elements located in two or more heat exchange zones, the flow rate of the heat exchange fluid in each of the two or more heat exchange zones can be controlled based on the sensed physiological parameters. Control of the flow rate includes, but is not limited to, independent control of the heat exchange fluid flow rate within each of the individual heat exchange elements.

In addition to controlling the heat exchange fluid flow rate, the present invention also includes controlling a temperature of heat exchange fluid within the heat exchange garment. Control of the temperature of the heat exchange fluid can also be based on the sensed physiological parameters. So, for example, when the heat exchange garment includes heat exchange elements located in two or more heat exchange zones, the temperature of the heat exchange fluid in each of the two or more heat exchange zones can be controlled based on the sensed physiological parameters. Control of the temperature includes, but is not limited to, independent control of the heat exchange fluid temperature within each of the individual heat exchange elements. In an additional embodiment, it is also possible to control both the flow rate and the temperature of the heat exchange fluid in each of the heat exchange zones based on the sensed physiological parameters.

In one embodiment, the present invention allows for the temperature of the body to be controlled (i.e., regulated) through heat exchange with the HD tissues of the body based on sensed parameters. For example, sensors may be located on one or more locations of the garment or elsewhere for providing temperature measurements to determine whether cooling/heating is needed at one or more locations of the body. By targeting the HD tissue regions for heat exchange, the present invention can provide a smaller, lighter and more efficient heat exchange garment as compared to presently available heat exchange suits. Such feedback control of the heat exchange that can take place between the heat exchange zones of the garment and the HD tissues regions adjacent the heat exchange zones will be further described herein with reference to the system of FIG. 7. In the example discussed above, the feedback control can be provided from physiological parameters sensed at a position on a distal extremity of the human body.

One particular position on the distal extremity used for controlling the body temperature in the present invention relies on the physiological mechanism of vessel response and blood flow change in one or more fingers under different temperature applications on the body surface and heat deficit in the body. The degree of finger vessel constriction in cold conditions, and vasodilation in warm conditions shows a direct relationship between status of finger blood flow and different levels of developing heat deficit/excess in the body (See Koscheyev et al., "Augmentation of Blood circulation to the fingers by warming distant body areas", Eur. J. Appl. Physiol (2000) 82:103–111; Koscheyev et al., "Thermoregulation and Heat Exchange in a Nonuniform Thermal Environment During Simulated Extended EVA" Aviat Space Environ Med 2000: 71:579–85; Ducharme M B, Tikuisis p (1994). Role of blood as heat source or sink in human limbs during local cooling and heating. J Appl Physiol 76:2084–2094; Ducharme M B, Van Helder W P, Radomski M W (1991). Tissue temperature profile in the human forearm during thermal stress and thermal stability. (J Appl Physiol 71:1973–1978).

This type of information can be used in the feedback control of the heat exchange garment of the present system. For example, when physiological parameters sensed from one or more fingers indicate a drop in temperature and/or heat flux, heat can be transferred to at least one heat exchange zones of the present invention. Heat delivered to the HD tissue region is also known to increase, lower and/or maintain finger temperature. This in turn helps to increase the comfort level of the person using the heat exchange suit of the present invention.

Alternatively, physiological parameters sensed from the finger may indicate an increase in temperature and/or heat flux, heat can be transferred from the at least one heat exchange zones of the present invention. Other combinations of heat transfer between the heat exchange zones and the HD tissues, as previously discussed, can also be controlled by the physiological parameters sensed from the finger.

Figure 3:
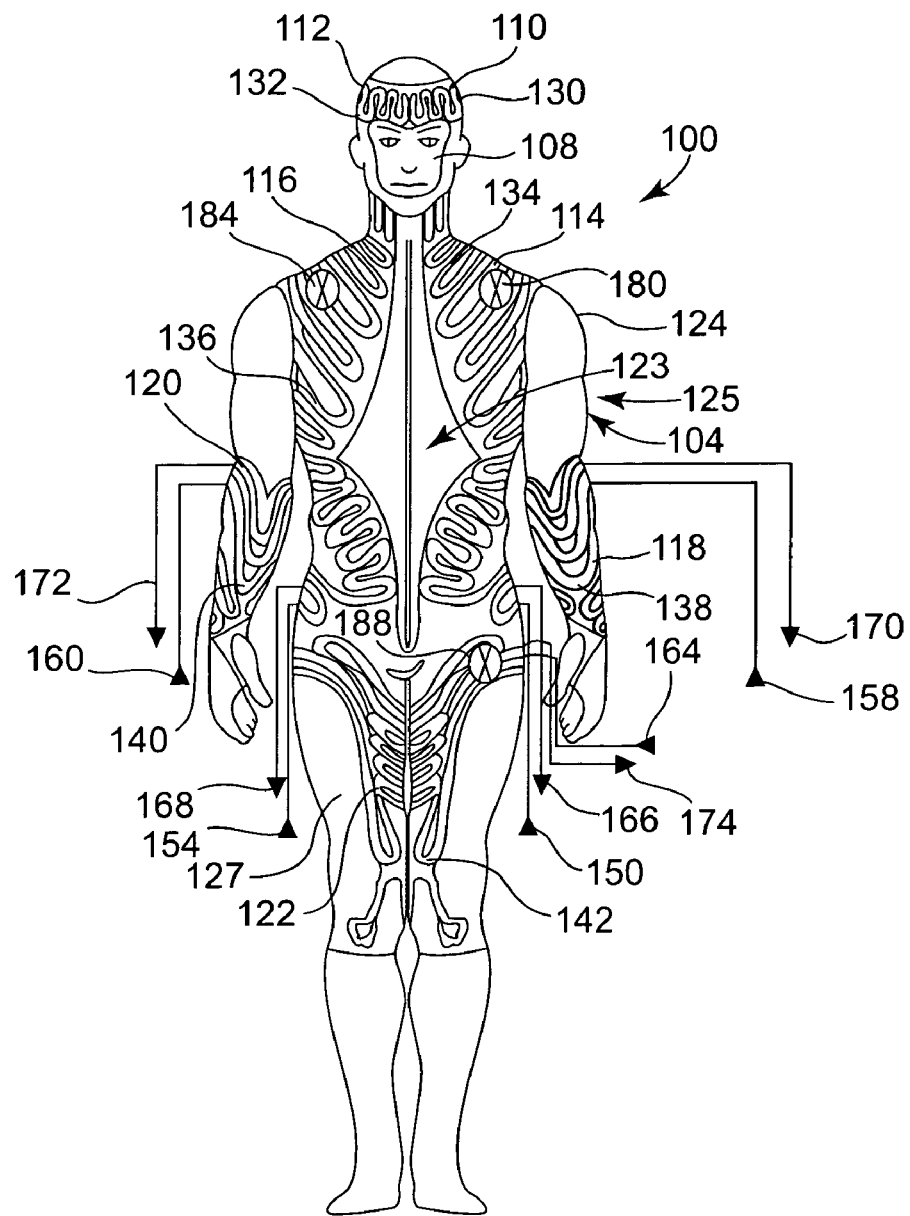
FIG. 3 is a schematic diagram illustrating a front view of a person wearing a heat exchange garment according to one embodiment of the present invention.

FIG. 3 is a schematic illustration of one embodiment of a heat exchange garment 100 according to the present invention. FIG. 3 shows an example of a front view of the heat exchange garment 100. The heat exchange garment 100 includes a support material 104. In one embodiment, support material 104 is defined to conform to at least a portion of a human body 108. Examples of suitable material for the garment 100 include, but are not limited to, woven or knitted fabrics. The woven or knitted fabrics can also include a flexible and/or stretchable component to allow the support material 104 to conform closely to the human body 108. Fabrics that include Lycra® are examples of suitable support materials for the present invention. Other suitable fabrics can include those with various percentages of polyester, cotton, nylon and Lycra®.

The heat exchange garment 100 also includes examples of heat exchange elements located in at least one heat exchange zones. For example, the heat exchange garment 100 includes heat exchange zones 110, 112, 114, 116, 118, 120, and 122. The heat exchange zones 110, 112, 114, 116, 118, 120, and 122 are located in regions of the support material 104 such that when the heat exchange garment 100 is worn on the human body 108 the heat exchange zones are positioned adjacent high density tissue sites of the human body 108. Examples of the high density tissue areas shown in FIG. 3 include a left forearm (zone 118) and a right forearm (zone 120); a left half of a lateral thoracic area and upper torso (zone 114) and a right half of the lateral thoracic area and upper torso (zone 116); a left half of an occipital and parietal head area (zone 110) and a right half of an occipital and parietal head area (zone 112), gluteal and medial inner thigh area and groin area (zone 122).

FIG. 3 also shows examples of one or more non-heat exchange zones that are defined in the support material 104. The non-heat exchange zones were previously discussed above. Examples of the non-heat exchange zones include, but are not limited to, areas or regions of the abdominal muscles (e.g., stomach) 123, deltoid muscle 124, bicep and triceps muscles 125, gluteus maximus muscle 126 (FIG. 4), and quadriceps muscle group 127. Other non-heat exchange zones are also present on the human body.

Each of the heat exchange zones 110, 112, 114, 116, 118, 120, and 122 also includes at least one heat exchange element 130, 132, 134, 136, 138, 140 and 142, respectively. The heat exchange elements (e.g., 130, 132, 134, 136, 138, 140 and 142) are located primarily only in the at least one heat exchange zones (e.g., 110, 112, 114, 116, 118, 120, and 122), where each of the at least one heat exchange zones are defined in regions of the support material 104 such that when the garment 100 is worn on the human body 108 the at least one heat exchange zones are positioned adjacent high density tissue sites of the human body 108.

In one example, each of the heat exchange elements 130, 132, 134, 136, 138, 140 and 142 is a length of tubing that is secured to the support material 104 of the heat exchange garment 100. For example the tubing can be secured to the support material 104 by sewing the tubing to an inside surface of the support material 104 of the heat exchange garment 100. Alternatively, the tubing can be secured to the support material 104 by integrating the tubing into and/or through the support material 104. Other methods of locating the tubing at positions on the support material are also possible (e.g., gluing).

In one embodiment, each of the heat exchange elements 130, 132, 134, 136, 138, 140 and 142 can include heat exchange fluid. Heat can be transferred between the heat transfer fluid and the high density tissues sites of the human body, as previously discussed. In one embodiment, the heat exchange fluid enters each of the heat exchange elements 130, 132, 134, 136, 138, 140 and 142 through an inlet port and leaves through an outlet port. In FIG. 3, inlet ports 150, 154, 158, 160, and 164 are shown for heat exchange elements 134, 136, 138, 140 and 142, respectively. Outlet ports 166, 168, 170, 172, and 174 are also shown for heat exchange elements 134, 136, 138, 140 and 142, respectively. Examples of heat exchange fluid include, but are not limited to, water, antifreeze type solutions and/or alcohols.

As discussed, each of the heat exchange zones of the present invention are defined to add or remove heat from the adjacent high density tissue. Adding or removing the heat can depend on one or more operating conditions of the present invention, along with the density of the heat exchange element in the heat exchange zone. For example, larger temperature differences between the heat exchange fluid and the adjacent high density tissue can lead to higher heat transfer rates. The temperature difference, however, must not be so large as to cause discomfort to the user. The flow rate of the heat exchange fluid can also be varied to produce different heat transfer rates. Furthermore, the density of the heat exchange elements can be tailored to each heat exchange zone. This can be based on the ability of the high density tissue to transfer heat more or less effectively as compared to other high density tissue areas.

The heat exchange garment 100 can further include one or more valves that are operatively coupled to the tubing of the heat exchange elements. For example, valves 180, 184 and 188 are shown located in heat exchange zones 114, 116, and 122, respectively. In one embodiment, valves 180, 184 and 188 are incorporated into the length of tubing for the heat exchange elements 134, 136 and 142. The valves can be used to control the flow of the heat transfer fluid in the tubing of the heat exchange elements. For example, the valves can be manually operated to position the valves in any number of positions so as to reduce, increase or stop the flow of the heat exchange fluid in the tubing of the heat exchange elements. Alternatively, the valves can be operated electronically, or by any other actuator that is capable of controlling the valves in any number of positions so as to reduce, increase or stop the flow of the heat exchange fluid in the tubing of the heat exchange elements.

Figure 4:
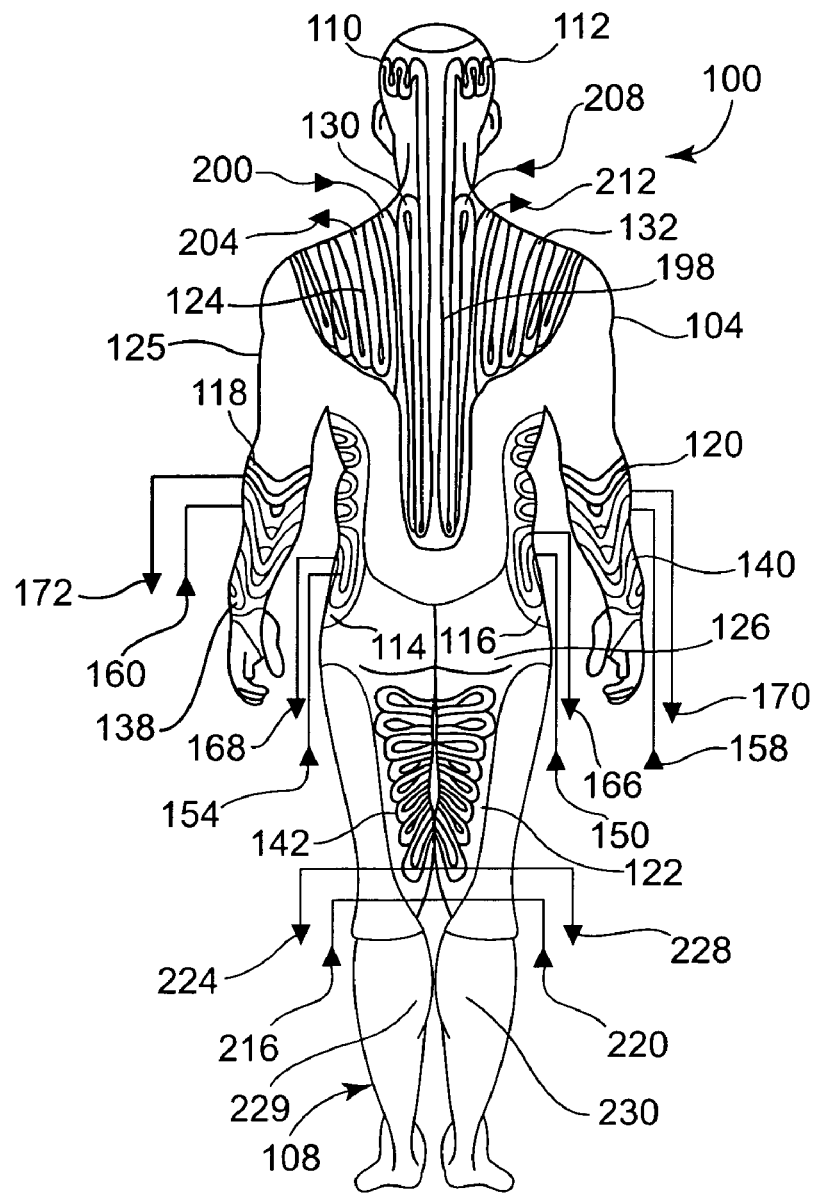
FIG. 4 is a schematic diagram illustrating a rear view of the person shown in FIG. 3 wearing a heat exchange garment according to one embodiment of the present invention.

FIG. 4 shows an additional schematic illustration of one embodiment of the heat exchange garment 100 according to the present invention. The FIG. 4 shows an example of a rear view of the heat exchange garment 100. The rear view of heat exchange garment 100 includes portions of heat exchange zones 110, 112, 114, 116, 118, 120, and 122, as discussed above. In this view, additional high density tissue sites can be see, such as the paraspinal areas 198 of the human body 108. FIG. 4 also shows inlet port 200 and outlet port 204 for the heat exchange element 130, and inlet port 208 and outlet port 212 for the heat exchange element 132.

In addition, FIG. 4 shows that heat exchange element 142 further includes inlet connection ports 216 and 220, and outlet connection ports 224 and 228. Connection ports 216, 220, 224 and 228 are defined to be connected to a heat exchange zone that can be positioned adjacent high density tissues on and around the left ankle and tibia/shin region 229 and the right ankle and tibia/shin region 230 of the human body 108 as shown, for example, in FIG. 5.

Figure 5:
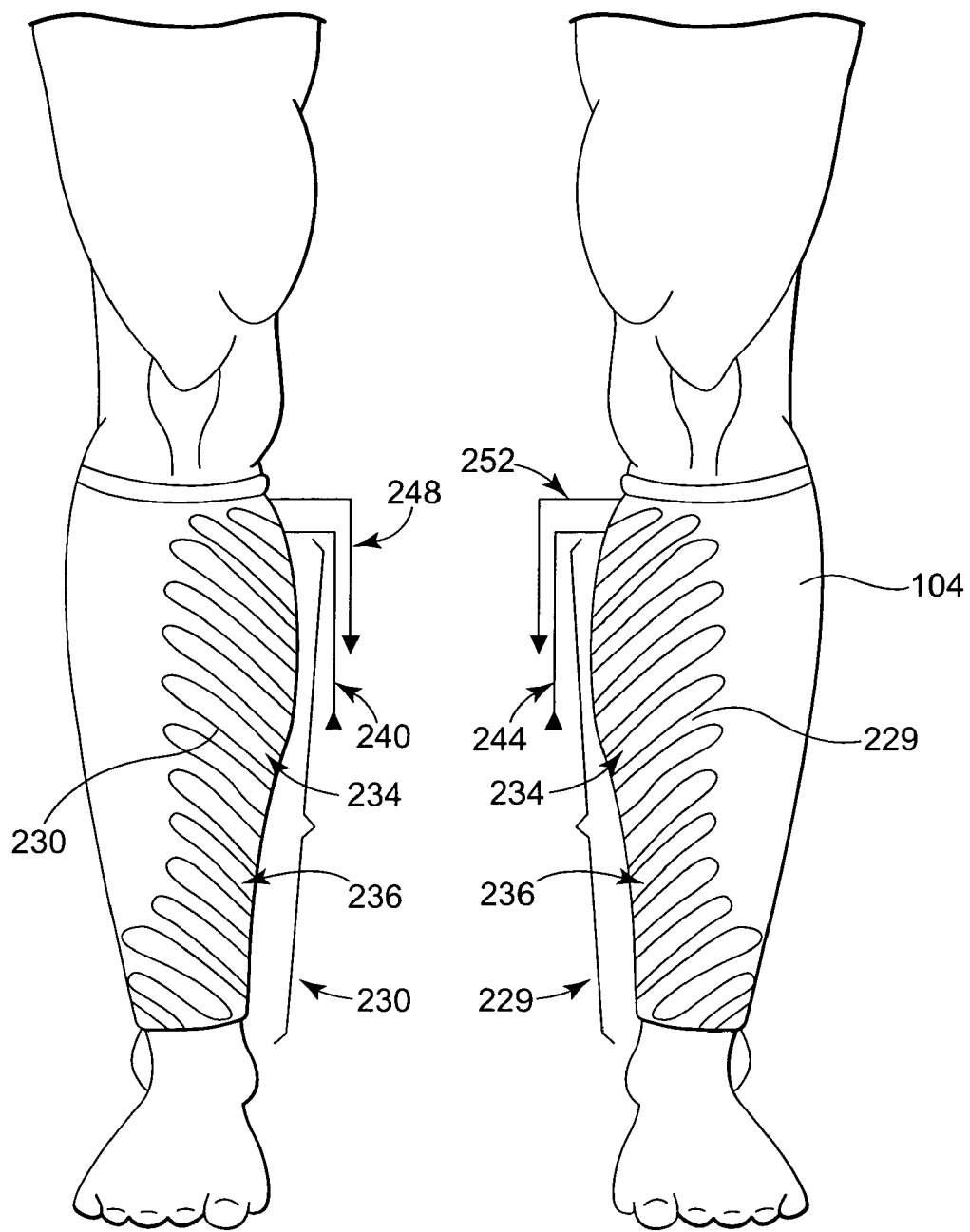
FIG. 5 is a schematic diagram illustrating a portion of a heat exchange garment according to one embodiment of the present invention.

FIG. 5 shows one example of a supplemental heat exchange zone 234 corresponding to both the ankle and shin (e.g., tibia bone) region for the heat exchange suit 100. The ankle and shin regions of the leg include HD tissue composed of, but not limited to, the tarsus and tibia bones, the calcaneal tendon, the soleus muscle (among many others), the posterior tibial and peroneal arteries, as well as portions of the great saphenous vein. The heat exchange zone 234 also includes a heat exchange element 236, which can be similar to those heat exchange elements already described. In addition, the heat exchange element 236 also includes inlet connection ports 240 and 244, and outlet connection ports 248 and 252. Note that the tubing is primarily adjacent HD bone structure of the tibia and tarsus along the inner portion of the calf and ankle.

In one embodiment, the heat exchange zone 234 is optionally connected to the to become part of the heat exchange garment 100. In one embodiment, these connection ports 240, 244, 248 and 252 allow the heat exchange element 236 to be operatively coupled to the heat exchange element 142 through inlet connection ports 216 and 220, and outlet connection ports 224 and 228. Heat exchange fluid moving through the heat exchange element 142 can then also be moved through the heat exchange element 236. Alternatively, the connection ports 240, 244, 248 and 252 of heat exchange zone 234 can be coupled to other inlet and outlet ports to allow for heat exchange fluid to move through the heat exchange element 236.

The heat exchange elements of the present invention can have any number of shapes and sizes, and can be constructed of any number of materials. For example, the heat exchange element can be tubing through which the heat exchange fluid can be moved. The tubing can have any number of profile shapes, including, but not limited to, round, oval, elliptical, or other shapes that would allow for increase in surface area of tubing. The tubing can also be constructed of any number of flexible polymeric materials, including, but not limited to, polyvinyl chloride, polyethylene, polypropylene, silicon. In one example, Tygon® tubing can be used for the heat exchange elements.

The inlet and outlet connections of the heat exchange elements can also be coupled in any number of ways. For example, fluid tight quick connect coupling mechanisms at each end of the inlet and outlet connections for the heat exchange elements can be used to releasably connect the tubing of the heat exchange elements to each other and/or to one or more heat exchange units, as will be discussed below. Other types of fluid tight connection mechanisms are also known.

FIGS. 3, 4, and 5 show only one example of the heat exchange garment 100 of the present invention. Modifications to the structure of the heat exchange garment 100 are certainly possible. For example, valves can be used to interconnect one or more of the heat exchange elements of the various heat exchange zones. In addition, two or more heat exchange zones through any number of planes of the body can share a common heat exchange element. This would reduce the number and complexity of inlet and outlet connections required. In addition, two or more valves could be placed at locations along the heat exchange elements used to heat and cool two or more heat exchange zones such that one or more zones could optionally receive reduced heat exchange fluid flow or be isolated from other heat exchange zones. As will be appreciated, the valves used to accomplish this feature will be bypass valves that will maintain a closed loop in the heat exchange zones such that the heat exchange fluid can continue to be moved through the system.

FIGS. 6A, 6B, 6C and 6D show a schematic illustration of one or more configurations for heat exchange gloves defined for use with the heat exchange garment of the present invention. Each of the one or more configurations for the heat exchange gloves can optionally be used in conjunction with the heat exchange garment 100, described above. In one embodiment, the heat exchange gloves of the present invention are defined to be positioned adjacent high density tissue of a right wrist joint of the hand and a left wrist joint of the hand of the human body.

The glove configurations are also intended to function to maintain hand/finger comfort and prevent chilled fingers. The problem of maintaining thermal stability of the hands and fingers can be addressed by the design of the gloves, where the design is based on anatomical and physiological principles of heat transfer by high density tissues and blood flow. Four different configurations of gloves are shown in FIGS. 6A, 6B, 6C, and 6D. Any one of the different configurations of gloves can be integrated into the heat exchange garment 100 of the present invention.

Figure 6A:
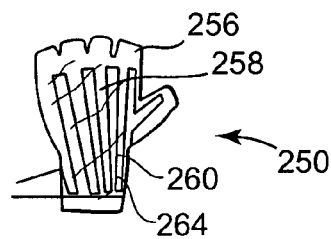
Figure 6B:
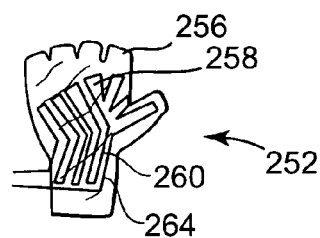

FIGS. 6A and 6B show a first glove configuration 250 and a second glove configuration 252 defined to fit a human hand, respectively. In one embodiment, the gloves include support material 256 that conforms to the human hand. The first glove configuration 250 and the second glove configuration 252 includes a heat exchange zone 258 that positions a heat exchange element 260 on the wrist and mid-palm area 264 of the human hand.

Figure 6C:
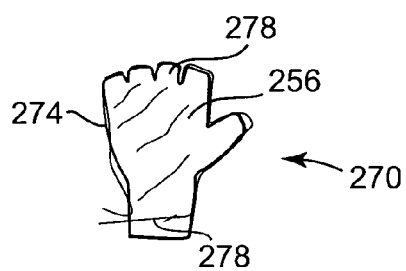
Figure 6D:
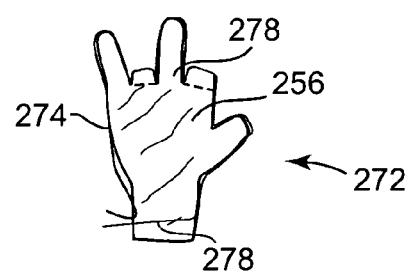

A third glove configuration 270 and a fourth glove configuration 272 are shown in FIGS. 6C and 6D. The third and fourth glove configurations includes a heat exchange zone 274 that positions a heat exchange element 278 on the proximal/lateral sides of the fingers precisely where there are major blood vessel paths, so the circulating blood can easily absorb heat and transport this heat to the distal phalanges. The glove configurations 250, 252, 270 and 272 can improve finger comfort and also significantly decrease the length of the heat exchange elements, e.g., tubes. This will decrease energy consumption and enhance the effectiveness of the heating system. Also, there can be less dissipation of heat because the heating elements are in direct contact with the vessel walls. By locating the heat exchange elements between the fingers (proximal/lateral part of phalanges), or strung around three fingers following the vessels paths, the rest of the fingers will be warmed between the heated fingers, therefore shortening the heat exchange elements. In addition, each of the glove configurations 250, 252, 270 and 272 include an "open" finger design, where at least two or more of the fingers of the person wearing the glove are not covered by the support material or heat exchange element.

In one embodiment, the heat exchange elements can be tubing, as described above, that allows heat exchange fluid to move through the heat exchange zones 258 and 274. Alternatively, the heat exchange elements can be electrical heating elements that are used to heat the heat exchange zones 258 and 274. When electrical heating elements are used, an electrical energy source can be included for powering the electrical heating elements.

FIG. 7 is a block diagram of a heat exchange system 300 according to one embodiment of the present invention. The heat exchange system 300 includes a heat exchange garment 310, as previously described. The heat exchange garment includes the support material and heat exchange elements, as discussed. At least one heat exchange zones and one or more non-heat exchange zones are shown in FIG. 7, where a first heat exchange zone 316 is defined to be positioned on and around the high density tissues of the head and torso, as described above. A second heat exchange zone 320 is also defined to be positioned on and around the high density tissues of the forearms, as described above. FIG. 7 also shows a third heat exchange zone 324 and a fourth heat exchange zone 328, where the third heat exchange zone 324 is defined to be positioned on and around the high density tissues of the gluteal and thigh, and the fourth heat exchange zone 328 is defined to be positioned on and around the high density tissues of the ankle and calves, as described above. Use of additional heat exchange zones is also possible, as discussed above.

The heat exchange system 300 also includes one inlet 334 and one outlet 338 for the heat exchange fluid moving through the heat exchange elements in the heat exchange zones 316, 320, 324 and 328. As previously discussed, the heat exchange elements are located primarily only in the at least one heat exchange zones. Control of the movement of the heat exchange fluid through the various heat exchange zones 320, 324 and 328 can be controlled through the use of one or more in-line valves 344, where each of the valves 344 can be independently controlled to change the flow rate of the heat exchange fluid through the various heat exchange zones 320, 324 and 328.

As discussed above, the valves 344 can be used to adjust flow of heat exchange fluid in different zones of suit. The valves 344 can be adjusted by the user through either manually adjusting the valve (e.g., turning a handle of the valve mechanism) or electronically, for example, through the use of one or more solenoids. Electronically adjusting the valves can be accomplished through the use of one or more switches adjacent to or located apart from the valve to adjust the flow of fluid through the valve. Positions for the valve include fully open, fully closed or any number of positions between the fully open and fully closed position. Alternatively, electronic adjustment of the valves may be accomplished through an automatic feedback control mechanism.

The heat exchange system 300 further includes at least one heat exchange unit 350 operatively coupled to the heat exchange elements of the heat exchange garment 310. In one embodiment, the at least one heat exchange unit 350 can be operatively coupled to the heat exchange elements of the heat exchange garment 310 through the inlet 334 and the outlet 338 for the heat exchange fluid. The heat exchange unit 350 may, for example, include a heat exchange conduit and an apparatus to move heat exchange fluid through the heat exchange conduit. In one embodiment, the heat exchange conduit may be a portion of tubing that includes a high thermal conductivity value so as to allow efficient heat exchange in the heat exchange unit 350. Examples of suitable materials for the heat exchange conduit include metals, such as copper, steel, aluminum, metal alloys, etc.

In one embodiment, the apparatus to move heat exchange fluid through the heat exchange conduit includes a pump. In one embodiment, the pump can be a variable speed pump to allow for various heat exchange fluid flow rates to be achieved. In addition, the heat exchange unit 350 can be used to add or remove heat energy from the heat exchange fluid moving through the heat exchange conduit. In one embodiment, the heat exchange unit 350 can include a heating mechanism and a cooling mechanism, where the heat exchange fluid moving through the heat exchange conduit can either add heat energy to or remove heat energy from the cooling source or to heating source, respectively. For example, electrical heating or cooling systems could be used to exchange heat with the heat exchange fluid in the heat exchange conduit. Alternatively, radiator type systems could be used in cooling the heat exchange fluid in the heat exchange conduit. Other cooling and heating source mechanisms are also possible. A power source 352 may also provided to supply electrical energy to the heat exchange unit, and other components of the heat exchange system 300. The power source 352 can include one or more batteries having one or more electrochemical cells for generating the electrical energy.

The heat exchange system 300 further includes at least one sensor. The example of FIG. 7 shows a single sensor 354. However, any number of sensors may be used. Preferably, the sensor 354, or other sensors, is defined to detect one or more physiological parameters from the human body, as previously discussed. However, other parameters other than physiological parameters may be sensed for use in controlling the system, e.g., temperature of surroundings, humidity thereof, etc.

As previously discussed, the sensor 354 can detect the one or more physiological parameters from one or more fingers of the human body. As discussed above, monitoring a temperature and a heat flux from the one or more fingers can provide an assessment of overall thermal status of the human body. In one embodiment, the sensor 354 can include a temperature sensor and one or more thermistors to measure the temperature and the heat flux at the finger. In one embodiment, the temperature sensor and the thermistors of the sensor 354 can be embedded in a ring that is worn on the finger.

The heat exchange system 300 also includes a feedback system controller 360 operatively coupled to the sensor 354, and or other sensors, and the heat exchange unit 350. The feedback system controller 360 may, for example, include a microprocessor and associated memory. In one embodiment, the microprocessor is used to execute executable programs stored in memory. These programs can include those for receiving signals from the sensor 354 and controlling the operation of one or more of the heat exchange units 350 and the valves 344 based on signals received from the sensor 354. For example, the feedback system controller 360 can be used to control the pump and/or heating and cooling operations of the heat exchange unit 350 to add or remove heat from the heat exchange fluid in the heat exchange conduit as a function of the one or more physiological parameters from the human body.

In one example, the feedback signals from the sensor 354 can be used to determine the amount of heat that is either being lost or gained by the body. Based on these amounts of heat, the feedback system controller 360 can be used to control the heating or cooling of the heat exchange fluid in the heat exchange unit 350 along with which combination of heat exchange zones in the heat exchange garment 310 need to be used to transfer the required amount of heating or cooling to the body. Control of the heat exchange zones can be accomplished through use of the valves 344. In addition, signals initiated from the sensor 354 can be used to indicate a life-threatening situation or minimally a tissue-damaging condition during which the feedback system controller 360 and the heat exchange unit 350 will attempt to balance the body heat of the person wearing the heat exchange garment so as to provide the best possible heating or cooling required during the emergency situation. One approach to balancing the body heat during the emergency situation is to isolate one or move heat exchange zones (i.e., stop or reduce flow of heat exchange fluid to the one or more heat exchange zones). Isolation of these zones effectively shortens the closed loop of the heat exchange fluid, thereby allowing the finite heating and/or cooling abilities of the heat exchange unit 350 to be better utilized in heating or cooling the core body areas.

The present invention provides various embodiments of protective heat exchange garments, heat exchange systems and methods for their operation in extreme environments. These include, but are not limited to, those encountered by firefighters, by military personal (especially those wearing biological/chemical/radiation protective suits), by divers wearing a diving suit, by miners, and by astronauts in outer space. Athletes for pre- or post-competition temperature regulation in extreme environments can also use the present invention. The present invention can also be used as a supplemental technology in the rehabilitation of stroke patients and other disabled groups such as those with multiple sclerosis.

All references cited herein are incorporated in their entirety as if each were incorporated separately. Documents cited herein, however, are not suggested to be prior art to the present invention. This invention has been described with reference to illustrative embodiments and is not meant to be construed in a limiting sense. Various modifications of the illustrative embodiments, as well as additional embodiments of the invention, will be apparent to persons skilled in the art upon reference to this description.

What is claimed is:

1. A method for controlling body temperature, comprising:
   providing a heat exchange garment configured to cover both high density tissue areas as well as non-high density tissue areas of at least a portion of a human body, the heat exchange garment comprising at least one heat exchange zone configured to correspond to one or more of the high density tissue areas of the human body, wherein each heat exchange zone comprises heat exchange elements for use in transferring at least heat to the human body; and limiting the location of heat exchange elements in the heat exchange garment to substantially only in the at least one heat exchange zone so as to provide selective heat exchange when the heat exchange garment is worn on the body in the one or more high density tissue areas of the body selected for having higher coefficients of conductivity relative to the non-high density tissue areas.

2. The method of claim 1, comprising positioning at least one heat exchange zone of the heat exchange garment to be adjacent one or more high density tissue areas of the body.

3. The method of claim 2, wherein positioning the at least one heat exchange zone comprises positioning the at least one heat exchange zone of the heat exchange garment to be adjacent one or more high density tissue and highly vascularized areas of the body.

4. The method of claim 2, comprising exchanging heat between the at least one heat exchange zone of the heat exchange garment and the adjacent high density tissue areas of the body.

5. The method of claim 4, wherein exchanging heat comprises cooling the adjacent high density tissue area with the at least one heat exchange zone of the heat exchange garment.

6. The method of claim 4, wherein exchanging heat comprises heating the adjacent high density tissue area with the at least one heat exchange zone of the heat exchange garment.

7. The method of claim 2, wherein exchanging heat comprises:
cooling a first adjacent high density tissue area with at least a first heat exchange zone of the at least one heat exchange zone of the heat exchange garment; and
heating a second adjacent high density tissue area with at least a second heat exchange zone of the at least one heat exchange zone of the heat exchange garment.

8. The method of claim 7, wherein the cooling of the first adjacent high density tissue area and the heating of the second adjacent high density tissue area occur substantially simultaneously.

9. The method of claim 4, wherein the method further comprises sensing one or more physiological parameters; and wherein exchanging heat comprises controlling at least one characteristic of a heat exchange fluid within a heat exchange garment based on the sensed one or more physiological parameters.

10. The method of claim 9, wherein sensing one or more physiological parameters comprises sensing one or more physiological parameters at a position on a distal extremity.

11. The method of claim 9, wherein sensing one or more physiological parameters at the position on the distal extremity comprises sensing one or more physiological parameters at a finger.

12. The method of claim 9, wherein controlling at least one characteristic of the heat exchange fluid comprises controlling a flow rate of heat exchange fluid within the heat exchange garment based on the sensed physiological parameters.

13. The method of claim 9, wherein controlling at least one characteristic of the heat exchange fluid comprises controlling a temperature of heat exchange fluid within the heat exchange garment based on the sensed physiological parameters.

14. The method of claim 9, wherein the heat exchange garment comprises heat exchange elements containing the heat exchange fluid and located in two or more heat exchange zones, and wherein controlling at least one characteristic of the heat exchange fluid comprises independently controlling a flow rate of heat exchange fluid within each of the heat exchange elements based on the sensed physiological parameters.

15. The method of claim 9, wherein the heat exchange garment comprises heat exchange elements containing the heat exchange fluid and located in two or more heat exchange zones, and wherein controlling at least one characteristic of the heat exchange fluid comprises independently controlling a temperature of heat exchange fluid within each of the heat exchange elements based on the sensed physiological parameters.

16. A method for controlling body temperature, comprising:
sensing one or more physiological parameters at a position on a distal extremity of a human body; and
controlling at least one characteristic of a heat exchange fluid within a heat exchange garment based on the sensed one or more physiological parameters, wherein the heat exchange garment is configured to cover both high density tissue areas as well as non-high density tissue areas of at least a portion of the body, wherein the heat exchange garment comprises a plurality of heat exchange zones configured to correspond to one or more high density tissue areas of a human body, wherein each of the plurality of heat exchange zones comprises heat exchange elements for use in exchanging heat with the human body, and further wherein the location of heat exchange elements in the garment are limited to substantially only in the plurality of heat exchange zones corresponding to one or more high density tissue areas so as to provide selective heat exchange when the heat exchange garment is worn on the body in the one or more high density tissue areas of the body selected for having higher coefficients of conductivity relative to the non-high density tissue areas.

17. The method of claim 16, wherein sensing one or more physiological parameters at the position on the distal extremity comprises sensing one or more physiological parameters at a finger.

18. The method of claim 16, wherein controlling at least one characteristic of the heat exchange fluid comprises controlling a flow rate of heat exchange fluid within the heat exchange garment based on the sensed physiological parameters.

19. The method of claim 16, wherein controlling at least one characteristic of the heat exchange fluid comprises controlling a temperature of heat exchange fluid within the heat exchange garment based on the sensed physiological parameters.

20. The method of claim 16, wherein the heat exchange garment comprises heat exchange elements containing the heat exchange fluid and located in two or more heat exchange zones of the garment, and wherein controlling at least one characteristic of the heat exchange fluid comprises independently controlling a flow rate of heat exchange fluid within each of the heat exchange elements based on the sensed physiological parameters.

21. The method of claim 16, wherein the heat exchange garment comprises heat exchange elements containing the heat exchange fluid and located in two or more heat exchange zones of the garment, and wherein controlling at least one characteristic of the heat exchange fluid comprises independently controlling a temperature of heat exchange fluid within each of the heat exchange elements based on the sensed physiological parameters.

22. The method of claim 16, wherein the method further comprises positioning heat exchange elements in at least one heat exchange zone of the heat exchange garment adjacent one or more high density tissue areas of a human body.

23. The method of claim 22, wherein positioning the at least one heat exchange zone comprises positioning the at least one heat exchange zone of the heat exchange garment to be adjacent one or more high density tissue and highly vascularized areas of the body.

24. The method of claim 22, wherein exchanging heat comprises heating the adjacent high density tissue area using the one or more heat exchange elements of the heat exchange garment.

25. The method of claim 22, wherein exchanging heat comprises cooling the adjacent high density tissue area using the one or more heat exchange elements of the heat exchange garment.

26. The method of claim 24, wherein exchanging heat comprises:
cooling a first adjacent high density tissue area with at least a first heat exchange element of the at least one heat exchange zone of the heat exchange garment; and
heating a second adjacent high density tissue area with at least a second heat exchange element of the at least one heat exchange zone of the heat exchange garment.

27. The method of claim 26, wherein the cooling of the first adjacent high density tissue area and the heating of the second adjacent high density tissue area occur substantially simultaneously.

28. A heat exchange garment, comprising:
a support material configured to cover both high density tissue areas as well as non-high density tissue areas of at least a portion of a body, wherein the support material is defined to conform to at least a portion of a human body, wherein one or more heat exchange zones and one or more non-heat exchange zones are defined in the support material; and
heat exchange elements located primarily only in the one or more heat exchange zones, wherein each of the one or more heat exchange zones are defined in regions of the support material such that when the garment is worn on the human body the one or more heat exchange zones are positioned adjacent high density tissue areas of the human body so as to provide selective heat exchange when the heat exchange garment is worn on the body in the high density tissue areas of the body selected for having higher coefficients of conductivity relative to the non-high density tissue areas.

29. The heat exchange garment of claim 28, wherein when the garment is worn on the human body the one or more heat exchange zones are defined to be positioned adjacent high density tissue of a left forearm and a right forearm of the human body.

30. The heat exchange garment of claim 28, wherein when the garment is worn on the human body the one or more heat exchange zones are defined to be positioned adjacent high density tissue of a left half of a lateral thoracic area and a right half of the lateral thoracic area of the human body.

31. The heat exchange garment of claim 28, wherein when the garment is worn on the human body the one or more heat exchange zones are positioned adjacent high density tissue and highly vascularized sites of the human body.

32. The heat exchange garment of claim 28, wherein when the garment is worn on the human body the one or more heat exchange zones are defined to be positioned adjacent high density tissue of a left half of an occipital and parietal head area and a right half of an occipital and parietal head area of the human body.

33. The heat exchange garment of claim 28, wherein when the garment is worn on the human body the one or more heat exchange zones are defined to be positioned adjacent high density tissue of paraspinal areas of the human body.

34. The heat exchange garment of claim 28, wherein when the garment is worn on the human body the one or more heat exchange zones are defined to be positioned adjacent high density tissue of a gluteal, a medial and an inner thigh area of the human body.

35. The heat exchange garment of claim 28, wherein when the garment is worn on the human body the one or more heat exchange zones are defined to be positioned adjacent high density tissue of a groin area of the human body.

36. The heat exchange garment of claim 28, wherein when the garment is worn on the human body the one or more heat exchange zones are defined to be positioned adjacent high density tissue of an upper torso area of the human body.

37. The heat exchange garment of claim 28, wherein when the garment is worn on the human body the one or more heat exchange zones are defined to be positioned adjacent high density tissue of a left ankle and calve region and a right ankle and calve region of the human body.

38. The heat exchange garment of claim 28, wherein when the garment is worn on the human body the one or more heat exchange zones are defined to be positioned adjacent high density tissue of a right wrist joint of a hand and a left wrist joint of the hand of the human body.

39. The heat exchange garment of claim 28, wherein the heat exchange elements comprises tubing containing heat transfer fluid for transferring heat between the heat transfer fluid and the high density tissues sites of the human body.

40. The heat exchange garment of claim 39, wherein the garment further comprises one or more valves operatively coupled to the tubing, wherein the valves control the flow of heat transfer fluid in the tubing of the heat exchange elements.

41. A heat exchange system, comprising:
a heat exchange garment comprising support material configured to cover both high density tissue areas as well as non-high density tissue areas of at least a portion of a body, wherein the support material is defined to conform to at least a portion of a human body and wherein one or more heat exchange zones and one or more non-heat exchange zones are defined in the support material, and further wherein heat exchange elements are located primarily only in the one or more beat exchange zones, wherein each of the one or more heat exchange zones are defined in regions of the support material such that when the garment is worn on the human body the one or more heat exchange zones are positioned adjacent high density tissue areas of the human body so as to provide selective heat exchange when the heat exchange garment is worn on the body in the high density tissue areas of the body selected for having higher coefficients of conductivity relative to the non-high density tissue areas;
at least one heat exchange unit operatively coupled to the heat exchange elements of the heat exchange garment, wherein the at least one heat exchange unit is operable to move heat exchange fluid through the heat exchange elements, and wherein the at least one heat exchange unit is operable to add or remove heat from the heat exchange fluid;

at least one sensor, where the at least one sensor detects one or more physiological parameters from the human body; and a feedback system controller operatively coupled to the at least one sensor and the at least one heat exchange unit, wherein the feedback system controller controls the at least one heat exchange unit to add or remove heat from the heat exchange fluid as a function of the one or more sensed physiological parameters from the human body.

42. The heat exchange system of claim 41, wherein the heat exchange garment comprises heat exchange elements located in two or more heat exchange zones that correspond to regions of the support material, wherein each of the two or more heat exchange zones are located in regions of the support material such that when the garment is worn on the human body the two or more heat exchange zones are positioned adjacent high density tissue sites of the human body.

43. The heat exchange system of claim 41, wherein the heat exchange elements comprise one or more tubes containing heat transfer fluid.

44. The heat exchange system of claim 43, wherein the system further comprises one or more valves operatively coupled to the one or more tubes, wherein the feedback system controller controls the one or more valves to adjust the flow of heat transfer fluid in the one or more tubes as a function of the one or more sensed physiological parameters.

* * * * *